United States Patent
Hung et al.

(10) Patent No.: US 9,486,402 B2
(45) Date of Patent: Nov. 8, 2016

(54) COMPOSITIONS CONTAINING BERBERINE OR ANALOGS THEREOF FOR TREATING ROSACEA OR RED FACE RELATED SKIN DISORDERS

(75) Inventors: Shuen-Iu Hung, Zhanghua (TW); Wen-Hung Chung, Nantou County (TW); Tse-Wen Chang, Taipei (TW)

(73) Assignee: Derman Biomedicine Co. Ltd, Tauyuan County (TW)

( * ) Notice: Subject to any disclaimer, the term of this patent is extended or adjusted under 35 U.S.C. 154(b) by 1126 days.

(21) Appl. No.: 13/379,604

(22) PCT Filed: Jun. 30, 2010

(86) PCT No.: PCT/CN2010/000983
§ 371 (c)(1),
(2), (4) Date: Mar. 13, 2012

(87) PCT Pub. No.: WO2011/000218
PCT Pub. Date: Jan. 6, 2011

(65) Prior Publication Data
US 2012/0165357 A1      Jun. 28, 2012

Related U.S. Application Data

(60) Provisional application No. 61/221,725, filed on Jun. 30, 2009.

(51) Int. Cl.
*A61K 9/14* (2006.01)
*A61K 31/4375* (2006.01)
*A61K 45/06* (2006.01)
*A61K 9/00* (2006.01)

(52) U.S. Cl.
CPC ......... *A61K 9/0014* (2013.01); *A61K 31/4375* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,440,465 B1 | 8/2002 | Meisner | |
| 6,482,839 B1 | 11/2002 | Thornfeldt | |
| 2002/0164386 A1* | 11/2002 | Meisner | 424/725.1 |
| 2006/0286054 A1 | 12/2006 | Gomez | |

FOREIGN PATENT DOCUMENTS

| | | |
|---|---|---|
| CN | 1 085 600 A | 4/1994 |
| CN | 1182788 A | 5/1998 |
| CN | 1923199 A | 3/2007 |
| DE | 20 2010 004750 U1 | 10/2011 |
| JP | 63179812 | 7/1988 |
| JP | H4-356424 * | 12/1992 |
| KR | 20030082200 | 10/2003 |
| WO | WO2004093876 A2 * | 11/2004 |

OTHER PUBLICATIONS

Leung et al. New insights into atopic dermatitis. J. Clin. Invest. (2004), vol. 113, pp. 651-657.*
Yamasaki et al. The molecular pathology of rosacea. J Dermatol Sci. (2009) vol. 55, p. 77-81. Epub May 29, 2009.*
Reuter et al., "Botanicals in Dermatology an Evidence-Based Review", Am J. Clin. Dermatol. 2010; 11 (4) pp. 247-267.
PCT International Search Report for PCT Application No. PCT/CN2010/000983, mailed on Oct. 21, 2010, 6 pages.
EP Search Report issued Nov. 27, 2012.
Third Part Submission in Corresponding Australian Application No. AU 2010268647 filed Jun. 30, 2010, Council of Scientific & Industrial Research issued Mar. 5, 2014.
Khan et al., vol. II Part II $19^{th}$ century AD, Kanpur, 1898 AD p. 5, formulation ID: AA26/06E; Formulation Name: Zimaad-Bara-e Damameel Wa Busoor.
Sodhala et al., Institute Baroda, Edn $1^{st}$ 1978 p. 123; Formulation ID RG9/263; Formulation Name: Rasanjan Gunah.
Abdullah et al., vol. III 13th Century AD Matba Amra, Cairo, Egypt 1874 AD p. 142; Formulation ID: MH6/221A; Formulation Name: Zimaad-e-Ausaj Barae Namlah.
Khan et al., vol. III $20^{th}$ Century AD Nadeem Yunus Printer / Sheikh Mohd Basheer & Sons, Lahore 1926 AD p. 390; Formulation ID: JA6/359X; Formulation Name: Raughan-c-kalonji.
Basavaraja; $1^{st}$ Reprint 2005 Time of Origin $15^{th}$ Century, p. 358; Formulation ID: VK1/929C; Formulation Name: Vatpatradi Lepa.
Majoosi et al., Part II $10^{th}$ Century AD Central Council for Research in Unani Medicine, 61-65 Institutional Area, Janak Puri, New Delhi 58, 2005 AD p. 123; Formluation ID: AH3/805B1; Formulation Name: Dawa Baraae Aasaar-e-Wajh.
Hrdaya; edn. $8^{th}$ 1998; time of origin $5^{th}$ Century p. 716; Formulation ID: RS23/1064; Formulation Name: Jivantyadi Malahara.
Yogaratnakarah; Edn. $8^{th}$ 2004 p. 236; Formulation ID: RG8/894; Formulation Name: Kusthadi Curna.
Livia Slobodnikova et al: "Antimicrobial activity of Mahonia aquifolium crude extract and its major isolated alkaloids", Phytotherapy Research, John Wiley & Sons Ltd. Chichester, GB, vol. 18, No. 8; Aug. 1, 2004, pp. 674,676, XP008158021.
Ju Qiang et al: "In vitro effects of the traditional Chinese medicine, berberine, matrine and baicalin, on the proliferation and lipid synthesis of immortalized human sebocyte SZ95", Zhonghua Pifuke Zazhi—Chinese Journal of Dermatology, Zhongguo Yixue Kexueyuan Pifubing Yanjiusuo, Manjing, CN, vol. 38, No. 11, Nov. 1, 2005, pp. 662-664, XP008158075.

(Continued)

*Primary Examiner* — Kendra D Carter
*Assistant Examiner* — Taina D Matos Negron
(74) *Attorney, Agent, or Firm* — Wood, Phillips, Katz, Clark & Mortimer

(57) ABSTRACT

The invention pertains to topical pharmaceutical formulations of berberine and its biologically equivalent analogs, such as palmatine and coptisine, for the treatment of rosacea and other red face-related skin disorders. The topical pharmaceutical formulations of this invention contain purified berberine as the primary active drug ingredient at concentrations higher than 0.1%. The invention also pertains to methods of treating rosacea and other red face related skin disorders, such as steroid-induced rosacea-like dermatitis, comprising the administration of topical pharmaceutical formulations that contain berberine or its biologically equivalent analogs, such as palmatine.

4 Claims, 2 Drawing Sheets

(56) References Cited

OTHER PUBLICATIONS

Seki T et al: "Effect of some alkaloids, flavonoids and triterpenoids, contents of Japanese-Chinese traditional herbal medicines, on the lipogenesis of sebaceous glands." Skin Pharmacology: The Official Journal of the Skin Pharmacology Society 1993, vol. 6, No. 1, 1993, pp. 56-60, XP008176201.

Examination Report for corresponding European Application No. EP 10 793 513.2 dated Jun. 1, 2015.

Office Action issued May 19, 2016 in corresponding Korean Application No. 10-2012-7002287.

Kim et al., "Berberine inhibits TPA-induced MMP-9 and IL-6 expression in normal human keratinocytes", Phytomedicine 15, 2008, pp. 340-347.

* cited by examiner

COMPOSITIONS CONTAINING BERBERINE OR ANALOGS THEREOF FOR TREATING ROSACEA OR RED FACE RELATED SKIN DISORDERS

CROSS REFERENCE TO RELATED APPLICATIONS

This application is a 35 U.S.C. 371 national stage application of International Application No. PCT/CN2010/000983, filed Jun. 30, 2010, which claims priority to U.S. provisional application No. 61/221,725, filed Jun. 30, 2009, the entire contents of which are incorporated herein by reference.

BACKGROUND OF THE INVENTION

1. Rosasea and its Major Symptoms

Rosacea is a chronic skin disease that manifests redness and swelling, primarily on the face, especially on the central facial area. Other areas affected include the scalp, neck, ears, chest, back and the eyes. Rosacea is characterized by facial flushing, erythema, telangiectasia, and inflammatory episodes with papules and pustules and, in severe cases, rhinophyma. Comedones are notably absent[1].

Patients with rosacea mostly have increased sensitivity of the facial skin and dry, flaking facial dermatitis, edema of the face, and persistent granulomatous papulonodules[2]. According to clinical and histopathologic features, the disease can be classified into 4 subtypes: (a) erythematotelangiectatic, (b) papulopustular, (c) phymatous, and (d) ocular, each with 3 grades of severity (mild, moderate, severe)[3]. The course of the disease is typically chronic, with recurrent remissions and relapses.

2. Other Red Face Related Skin Disorders

Rosacea is the most common red face skin disorder. Other red face related skin disorders, which share symptomatic similarities and probably pathological causes, include acne vulgaris, seborrheic dermatitis, photodermatitis and contact dermatitis. These red face related conditions may range from feelings of heat and sensitivity to flushing or burning with intense sensitivity[4]. Patients with rosacea and other red face related skin disorders often exhibit extreme sensitivity to environmental and topical factors[5]. Steroid-induced rosacealike dermatitis (or steroid rosacea) is a papular or pustular lesions with erythematous and edematous base with or without telangiectasia, which is caused by prolonged application of topical steroids to the face or as a rebound condition after discontinuation of topical steroids[6,7] (Chen A Y Zirwas M J, 2009; Lee D H, Li K, Suh D H 2008). EGFR inhibitors, such as cetuximab, erlotinib, gefitinib, cause acneiform dermatitis on face or other skin area, including papulopustular reaction, erythema, telangiectasias, and flushing in 30 to 90% of patients and may also superinfected with bacteria, such as *staphylococcus aureus*[8,9] (Wollenberg A, Kroth J et al, 2010; Lacouture M E, Maitland M L et al, 2010).

3. Pathogenesis of Rosacea

The etiology of rosacea is not well understood. Various factors have been suggested to contribute to the development and manifestation of rosacea. None of them, however, has been definitely confirmed[1].

3.1. Genetic Contribution

Earlier studies have indicated genetic predisposition to flushing, the earliest manifestation of facial rosacea[10]. Additionally, glutathione S-transferase MU-1 (GSTM1) and glutathione S-transferase theta 1 (GSTT1) null genotype has been reported to be associated with an increased risk of rosacea[11].

3.2. Inflammation and Innate Immune System

As rosacea progresses, inflammatory lesions become evident. Unlike acne vulgaris, inflammatory rosacea is not a bacterial disease of the pilosebaceous unit. Comedones are usually not present, and only normal bacterial flora is identified in skin samples taken from rosacea patients[12]. The inflammatory stage of rosacea can be regarded as a form of chronic sterile cellulitis[13]. While the presence of microorganisms has been examined as a potential contributing factor to rosacea, results have been inconclusive[1]. *Demodex folliculorum* mites are considered as commensal and do not play a significant pathogenic role in rosacea, although an inflammatory reaction to the mites may aggravate symptoms[14].

Yamasaki et al found an abnormally high level of cathelicidins by histopathological staining in skin lesions from patients with rosacea. Human epidermal keratinocytes stimulated by cathelicidin peptides were found to increase the release of IL-8. Injection of cathelicidin peptides into the skin of mice caused inflammatory changes with increased neutrophil infiltration and microvessels characteristic of the skin disorder of rosacea in humans[15]. Cathelicdins possibly have dual roles in immunity because it can both kill microorganisms and stimulate host inflammatory responses such as inducing IL-8 release[16]. Other inflammatory cytokines found to be increased in rosacea include IL-1alpha and transforming growth factor beta-2[17,18].

3.3. Vascular Mediators

Inflammatory mediators may be responsible for the vasodilation seen in rosacea patients. For example, substance P, histamine, serotonin, bradykinin, or prostaglandins have been suggested[19]. Smith et al has reported an increased expression of vascular endothelial growth factor and its receptors in rosacea[20].

4. Current Management of Rosasea

A number of antibiotics, such as tetracycline and doxycycline have been used in treating rosacea. It has been suggested that such antibiotics render anti-inflammatory rather than antimicrobacterial effects. However, other anti-inflammatory agents are not effective in treating rosacea. Immunosuppressive agents such as corticosteroids often worsen the inflammatory condition of rosacea[1].

Topical metronidazole and certain systemic antibiotics are often used as first-line therapy for rosacea. Oral tetracycline, doxycycline, and minocycline are commonly used for treating rosacea. The efficacy of oral antibiotics is probably due more to anti-inflammatory rather than to antibiotic effects[21]. Azelaic acid 15% gel was approved by FDA of USA in 2002 for the topical treatment of mild to moderate rosacea[22]. Other traditional topical agents that have been used in a "off label" fashion include clindamycin, sulfacetamide and sulfur, but their mechanism is not well understood.

5. The Use of Berberine in Non-Skin Disorders

Berberine (Natural Yellow 18, 6-dihydro-9,10-dimethoxybenzo(g)-1,3-benzodioxolo (5,6-a) quinolizinium) is an isoquinoline alkaloid present in herb plants, such as coptis (*Coptidis rhizome*), phellodenron, *Scutellaria baicalensis, Mahonia aquifolium* and berberis[23]. Berberine and its derivatives have been found to have antimicrobial and antimalarial activities. It can act against various kinds of pathogens such as fungi, saccharomycete, parasite, bacterium and virus[24]. Berberine has been found to have other potential benefits. For example, it may have potential to treat high blood cholesterol, cardiovascular disease, diabetes, and tumor[25].

Berberine also has anti-inflammatory function, yet the exact mechanism is unknown. Recently, some researcher reported that the anti-inflammatory mechanism of berberine is mediated through cyclooxygenase-2 (COX-2) pathway, since COX-2 plays a key role in the synthesis of prostaglandins, which is elevated in inflammation[26]. Berberine is used as an ingredient in some eye drop solution or eye ointment for the treatment of tracoma[27].

6. The Use of Berberine in Skin Disorders

U.S. Pat. No. 6,440,465 pertains to topical skin formulations of glucosamine in an emollient base which contains berberine for the treatment of psoriasis[28]. Patent application #20050158404 pertains to a nutritional product, dietary supplement or pharmaceutical composition which contains vitamin A, vitamin E, selenium, vitamin B6, zinc, chromium, and a herbal source of berberine for the treatment of acne in oral administration[29]. U.S. Pat. No. 6,974,799 relates to topical compositions comprising a tripeptide (N-palmitoyl-Gly-His-Lys) and a tetrapeptide (N-palmitoyl-Gly-Gln-Pro-Arg) for the treatment of visible signs of aging including wrinkles, stretch marks, dark circles[30]. The formulation may contain additional ingredients, including berberine. In these inventions, berberine is included as one of the many ingredients and its concentration is not specified.

Patent application #20040146539 relates to topical neutraceutical compositions with body slimming and tone-firming anti-aging benefits that may be used to treat skin aging, skin wrinkle, skin exfoliating, acne, rosacea and other skin problems[31]. The composition of this invention includes antimicrobial agents selected from several agents including berberine. In these neutraceutical compositions, berberine is included as one of the many ingredients and its concentration is not specified. There has been a 10% *Mahonia aquifolium* cream (Relieva™, Apollo Pharmaceutical Canada Inc) containing 0.1% berberine for the treatment of psoriasis[32].

The therapeutic effect of berberine in treating rosacea and other red face-related skin disorder is unknown. Until now, there is no direct evidence suggesting that berberine can improve the symptoms of rosacea.

DESCRIPTION OF THE INVENTION

There is a need for an effective therapy for the treatment of rosacea and other related skin disorders with minimal side effects. The present invention pertains to topical pharmaceutical formulations that are effective and safe in treating rosacea and other red face related skin disorders, such as acne, seborrheic dermatitis, contact dermatitis and photodermatitis. This invention recognizes the deficiency in currently available topical pharmaceutical formulations or experimented formulations that contain berberine as a component, and improves over this deficiency.

There are lines of evidence that indicate that berberine is a drug active ingredient in animal studies and human clinical trials of berberine, either with purified berberine or formulations containing berberine herbal extract. In many disease indications, such as in the treatment of bacterial and fungal infections and cardiovascular diseases, statistically significant efficacy results of berberine have sometimes been obtained. In the trials on psoriasis with formulations containing berberine-rich extract, efficacious results were also obtained, although the efficacy of berberine in psoriasis has not been accepted. These results suggest that berberine can act on molecular targets and cause modifications in certain molecular pathways and cellular functions, such as described in the background section in this patent application.

It has been clearly shown in the pharmacological studies of numerous pharmaceutical compounds that a pharmaceutically active compound must be present in the body or affected tissues above certain threshold concentrations for the drug to achieve meaningful biological and pharmacological effects and hence therapeutic effects in the treated subject. In herbal medicinal preparations that contain the extracts of one or multiple plant(s), many active drug ingredients are present. In most treatments using herbal preparations either in an oral or topical route, the individual drug ingredients are present at sub-threshold concentrations in the body or affected tissues of a treated subject. However, several compounds from the same or different plants may act on the same molecular target or several compounds from the same plant or different plants may act on different molecular targets in the same biological pathway. As a result, the various compounds acted concertedly to cause a meaningful biological and pharmacological effect and hence therapeutic effect.

When a herbal pharmaceutical preparation fails to cause a therapeutic effect in a treated subject, it is likely that an otherwise pharmacologically active compound contained therein is present at too low a concentration in the treated subject and that the compound by itself or in combination with compounds in the preparation fail to cause a meaningful biological and pharmacological effect. In fact, many important drug compounds (single chemical entities) have been identified and isolated from plants that are used in herbal preparations. With these pure compounds, therapeutic efficacy often exceed that is achievable with the herbal preparations that contain the compounds.

Topical herbal pharmaceutical formulations that include berberine-rich plant extracts have been used for centuries in the treatment of various ailments, including a variety of skin disorders, such as psoriasis, acne, eczema, etc. These topical herbal preparations have achieved variable results. In some of those preparations, berberine-containing extract consists of about 10% of the various components used to constitute the formulation. It has been estimated that the berberine compound in those topical total preparations accounts approximately 0.1% (w/w) of the finished formulations[32].

Based on the above rationale, we have investigated in vitro the effects of berberine at various concentrations on biological pathways that may be involved in the pathogenesis of rosacea. Based on those results and the rationale described above, we have developed chemically defined topical pharmaceutical formulations that contain berberine at defined percentages that are higher than the concentrations of berberine in traditional herbal berberine-containing pharmaceutical formulations. We then tested those formulations on affected skin area on patients with rosacea. Our findings indicate that topical pharmaceutical formulations containing berberine above 0.1% (w/w) can achieve efficacious and tolerable results in treating rosacea and related sensitive red face disorders.

Analogs of Berberine

The structure of berberine (5,6-dihydro-9,10-dimethoxybenzo(g)-1,3-benzodioxolo (5,6-a) quinolizinium) is shown below:

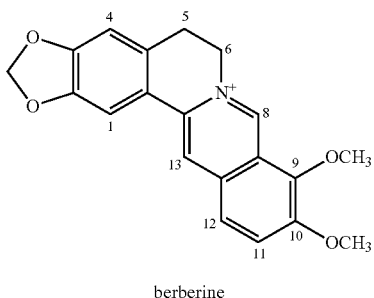 [SMILES: COc1ccc2cc3[n+](cc2c1OC)CCc1cc2c(cc1-3)OCO2]

berberine

Several protoberberine alkaloids can be prepared with variable biological activity similar to berberine, such as: jatrorrhizine, palmatine, coptisine-, 9-demethylberberine, 9-demethylpalmatine, 13-hydroxyberberine, berberrubine, palmatrubine, 9-O-ethylberberrubine-, 9-O-ethyl-13-[−]ethylberberrubine, 13-methyldihydroberberine N-methyl salt, tetrahydroprotoberberines, and their N-methyl salts, 13-Hexylberberine, 13-hexylpalmatine and 9-lauroylberberrubine chloride[33,34].

Palmatine is present in plants of various families, most notably in the rhizomes of *Fibrarurea Tinctoria Lour*. Palmatine is an isoquinoline alkaloid and formulations containing palmitine have been broadly used in China for the treatment of gynecological inflammation, bacillary dysentery, enteritis, respiratory tract infection, urinary infection. Additionally, palmatine has the function of anti-arrhythmia, antisepticise, bacteriostasis, and anti-viral activities. Palmatine can be also used as a compound in anti-tumor drug screening[35]. There has been a palmatine-containing pharmaceutical as topical hair growth inhibitor (Keramene, Divine Skin Solutions D S Laboratories Keramene Body Hair Minimizer).

Coptisine is an alkaloid found in Chinese goldthread (*Coptis chinensis*). It is used in Chinese herbal medicine along with the related compound berberine for treating digestive disorders caused by bacterial infections. Coptisine also exhibits some significant inhibition on tumor growth. Coptisine has been shown in vitro to be cytotoxic on human tumor colon cell line[36], human hepatoma and leukaemia cell lines[37].

In our studies, we have also investigated in vitro and in vivo the effects of palmatine, and coptisine at various concentrations on biological pathways that may be involved in the pathogenesis of rosacea. Based on those results and the rationale described above, we have also developed chemically defined topical pharmaceutical formulations that contain palmatine or coptisine at defined concentrations. These formulations could achieve efficacious and tolerable results in treating rosacea and related sensitive red face disorders.

Example 1

Effects of Berberine on Inhibiting Cathelicdin Peptides-Induced Cytokine Secretion by Human Keratinocytes (In Vitro Assay)

For our in vitro study, berberine (Sigma, St. Louis, Mo., USA) was dissolved in water, methanol, ethanol or dimethyl sulfoxide (DMSO). Normal human keratinocytes (Invitrogen, CA, USA) were grown in EpiLife medium (Invitrogen, CA, USA) supplemented with 0.06 mM $Ca^{+2}$, 1% EpiLife defined growth supplement, and 1% penicillin/streptomycin (Invitrogen, CA, USA). Cells were grown at 37° C. in a humidified atmosphere of 5% $CO_2$ and 95% air. The human keratinocytes were cultured to confluence and treated with synthetic cathelicidin peptides (LL-37) (6.4 μM) for 16 h to induce inflammatory response similar to that observed in rosacea. Some of the cathelicidin-treated keratinocyte cultures were co-incubated with berberine of concentrations from 1.25 μg/ml to 12.5 μg/ml. The keratinocytes cultures treated with cathrlicidin or cathrlicidin with 1% ethanol and without berberine were used as negative controls. Supernatants were collected and placed in a sterile 96-well plate for ELISA of interleukin-8 (IL-8), interleukin-1 alpha (IL-1 alpha), and venous epithelial cell growth factor (VEGF) in accordance with the manufacturer's instructions (R&D Systems, MN, USA).

The result showed that cathelicidin can induce IL-8, IL-1 alpha and VEGF release from cultured human keratinocytes. The inhibitory effect of berberine on the release of IL-8 (FIG. 1A), IL-1 alpha (FIG. 1B) and VEGF (FIG. 1C) was examined by adding different concentrations (0~12.5 μg/ml) of berberine in the culture medium. There was 31.4%, 24.9% and 29.1% decrease of the release of IL-8, IL-1 alpha and VEGF respectively, when cathelicidin-stimulated keratinocytes treated with 1.25 μg/ml berberine comparing to cathelicidin peptide-treated with 1% ethanol control ($P<0.05$). These results showed that berberine can significant inhibit cathelicidin induced inflammatory response in a dose-dependent manner, especially when the concentration of berberine was larger than 6.25 μg/ml, indicating that berberine has anti-inflammatory activity against cathelicidin-induced release of cytokines, which were related to rosacea.

Example 2

Preparation of Topical Pharmaceutical Formulations Containing Purified Berberine and Palmatine at Defined Percentages Based on the rationale described above, the topical berberine-containing pharmaceutical formulations of this invention have one key feature: it contains purified berberine at defined percentages that are higher than can be obtained in previous formulations using extracts of berberine-rich plants. The ranges of concentrations were subjected to tests in animal model studies and human clinical studies.

For our studies on animal models and human patients, purified berberine was dissolved in 100% ethanol, and then water was added to reach a desired concentration of berberine in the final solution. In the gel formulation, for example, 0.1% or 0.2% berberine was prepared in 10% ethanol. The solution or gel formulation were capped and stored at 4° C. until use. The results of our studies in animal models and human patients with rosacea indicate that the concentration of berberine in the formulation should be 0.1% or higher, in order to achieve consistently satisfactory results. These concentrations are higher than previously prepared topical berberine-containing formulations using berberine-rich plant extract.

Experiments are on going to prepare formulations in the form of an ointment, gel, cream, lotion, or spray, which are more suitable for use for clinicians and patients. In the topical pharmaceutical formulations of our invention, berberine or a biologically equivalent analog of berberine (e.g. palmatine and coptisine) is the only or primary active drug compound. The purified palmatine used for our studies is dissolved in 100% water, and then diluted to reach in the final solution or gel formulation with defined palmatine concentrations, for example, 0.02%, 0.1%, or 0.2% of palmatine.

However, improved or modified formulations may include additional ingredients for increased solubility of berberine or its analogue, emulsification, lubrication, antibiotic activity, or hydration.

One preferred embodiment of our invention to increase the solubility of berberine or a biological equivalent analog of berberine is to add glycerol into the formulation. One embodiment of our invention to increase the antibiotic activity of the formulation is to add plant extract that has been shown to have antibiotic activity. One embodiment to enhance the hydration property of the topical formulation of our invention is to add hyaluronic acid.

Example 3

The Effects of the Topical Pharmaceutical Preparation of this Invention on a Mouse Model of Rosacea The animal model of rosacea: the animal model of rosacea was adopted from previous reported[18]. Briefly, BALB/c and C57BL/6 mice, shaved 24 h before treatments, were injected subcutaneously on the back with 40 µl of cathelicdin peptide (320 µM) twice a day. Forty-eight hours after the initial injection (four injections in total), erythema and edema were observed on the injected site mimicking the clinical features of rosacea.

In our experiments, cathelicidin-injected mice were treated with or without topical berberine twice a day to observe the effect of berberine on reducing inflammation. The results showed that mice given subcutaneous injections of cathelicidin peptides induced erythema and vascular dilatation in the skin, which resembled clinical features of rosacea after 48 h. The cathelicidin-injected mice were then divided into 2 groups, which were treated with berberine (n=3) or not treated with berberine (n=3; as controls), respectively, for a subsequent 2 days. The topical formulation containing 0.1% berberine was applied on the cathelicidin-induced lesions twice a day. The erythematous or inflammatory lesions lasted for more than 7 days in the control group. At the 4$^{th}$ day, erythema and vascular dilatation were significant reduced in the berberine treated group comparing to controls. These results indicate that topical berberine can reduce the inflammatory reaction induced by cathelicidin in vivo.

Example 4

A Human Clinical Study Investigating the Efficacy of the Topical Pharmaceutical Formulation of this Invention on Patients with Rosacea Method: an open-label clinical study was carried out to determine the efficacy of the topical berberine formulations of this invention for the treatment of rosacea and related skin disorders. Patients included in this study were diagnosed by dermatologists to have clinically defined rosacea. All patients were given 0.1% berberine gel twice a day for 6 weeks. At the time points of treatment initiation, and 2-weeks and 6-weeks after treatment, the patients were evaluated for their rosasea symptoms. The patients were not allowed to use other medications, including antibiotics, for their skin conditions. Only oral antihistamines were allowed for relief of pruritus symptoms.

To evaluate the efficacy of treatment, the standard grading system for rosacea developed by the National Rosacea Society Expert Committee on the Classification and Staging of Rosacea was used[3]. Additionally, the investigator's global assessment (IGA) and overall erythema severity of the patients were scored at week 0, week 2, and week 6 of berberine therapy. The IGA was expressed according to a 7-point scoring system with a range of 0 (clear) to 6 (severe). The severity of overall facial erythema and telangiectasia, respectively, was graded as 'none', 'mild', 'moderate', or 'severe' with scores from 0 to 3. The grading system used to assess overall facial erythema severity was described previously[38].

Results: a total of 20 patients with rosacea (18 females and 2 males) were enrolled in this study. The mean age of the study population was 43.3 (19-85) years. The mean duration of rosacea prior to berberine treatment was 4 (1-24) years. Among the 20 patients with rosacea, 13 cases were of erythematotelangiectatic type (65%), 7 cases papulopustular type (35%), and 5 cases (25%) phymatous type.

According to the 7-point score system, IGA score of rosacea at baseline (initiation of treatment) was 4.1±1.3. This score decreased to 2.6±0.9 at week 2, then 1.6±0.8 at week 6. The difference of IGA scores between week 0, week 2, and week 6 was statistically significant (W2 vs W0: paired t test P<0.0001; W6 vs W0: paired t test P<0.0001). At the beginning of treatment, the majority of patients (95%) had grading from mild to moderate (3) to severe (6). By the end of treatment, 19 of the 20 patients (95%) had a mild (2) to clear (0) rating.

The overall erythema severity evaluated by the investigator was 2.35±0.6 at the beginning of treatment, 1.5±0.5 at week 2, and 0.95±0.4 at week 6. The improvement at week 2 or week 6 was statistically significant (W2 vs W0: paired t test P<0.0001; W6 vs W0: paired t test P<0.0001). At the beginning of treatment, the majority of patients (95%) had erythema rating from moderate (2) to severe (3). By the end of treatment, 19 of the 20 patients (95%) had a mild (1) to none (0) erythema rating.

Safety and tolerability: There was no serious adverse event during the study. Only 2 cases (10%) had transient itchy/stinging sensation in the area of topical medication, but were tolerable without discontinuation of study.

Example 5

Topical Berberine is Effective for the Treatment of Steroid-Induced Rosacealike Dermatitis, as Well as EGFR Inhibitors Induced Acneiform Dermatitis We also studied the 0.1% berberine gel on 10 patients with steroid-induced rosacealike dermatitis, 5 patients with EGFR inhibitors induced acneiform dermatitis, used in twice a day for 6 weeks. All 15 patients showed similar effective and tolerated response as observed with rosacea.

Example 6

Palmitine Showed Efficacy for the Treatment of Rosacea or Red Face Disorders

We also studied topical formulation containing palmatine at 0.02% (w/w) on 10 patients with rosacea and related red face disorders. All 10 patients showed similar effective and tolerated response as observed with berberine.

Conclusion Made from the Examples

In vitro culture studies have demonstrated that berberine exhibits anti-inflammatory effects by inhibiting cathelicidin-induced IL-8, IL-1 alpha and VEGF production by human keratinocytes. Since inflammation is involved in the pathogenesis of rosacea and related skin disorders, the anti-inflammatory effects of berberine may account for its clinically beneficial effect in rosacea and related inflammatory skin disorders.

The results of our clinical studies have shown that the topical pharmaceutical formulations of this invention containing purified berberine at concentrations higher than 0.1% or palmatine at concentrations higher than 0.02% can be efficacious, safe and well tolerable for the treatment of rosacea and red skin related disorders, such as acne, contact dermatitis, seborrheic dermatitis and photodermatitis, steroid-induced rosacealike dermatitis, and EGFR inhibitors induced acneiform dermatitis.

REFERENCES CITED

Figure 1:
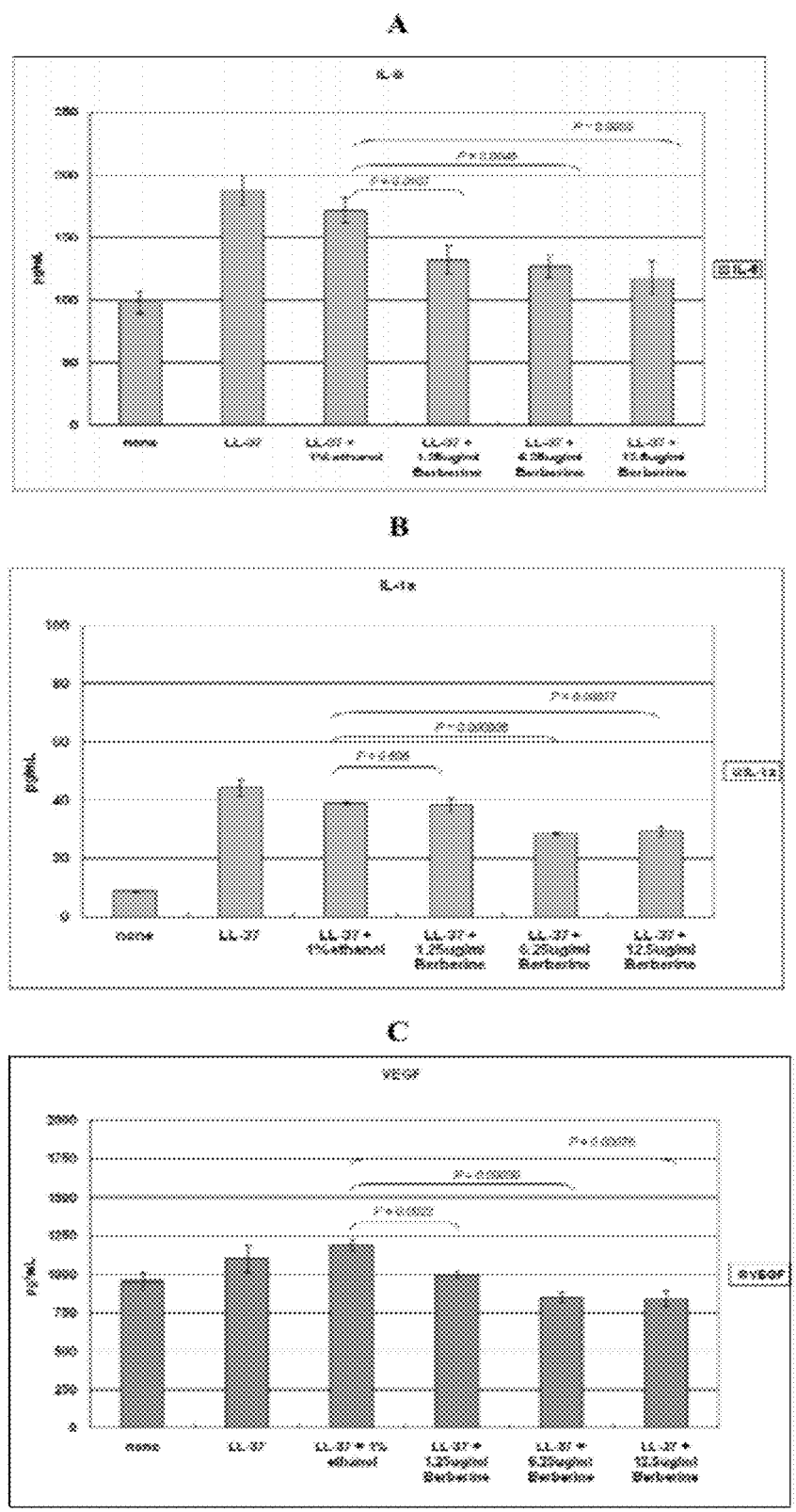
FIG. 1. Berberine inhibited cathelicidin peptide (LL-37)-induced IL-8, IL-1alpha and VEGF release from human keratinocytes. Keratinocytes were stimulated by cathelicidin peptide (LL-37), and the release of IL-8 (FIG. 1A), IL-1 alpha (FIG. 1B) and VEGF (FIG. 1C) by the keratinocytes was evaluated by ELISA assay.
Figure 2:
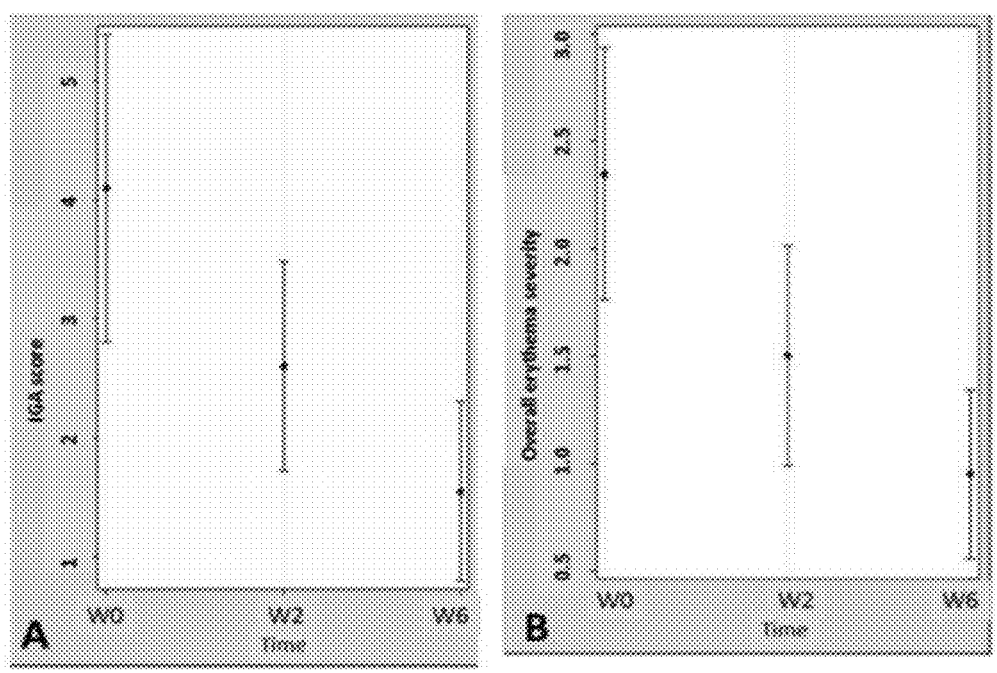
FIG. 2. A. Investigator's global assessment scores at the beginning of berberine treatment and at 2 weeks and 6 weeks of treatment. B. Overall erythema severity scores at the beginning of topical berberine treatment and at week 2 and week 6 of treatment

1. Plewig G, Jansen T. Rosacea. In: Freedberg I M, Eisen A Z, Wolff K, et al., eds. Dermatology in General Medicine. 6th ed. New York, N.Y.: McGraw-Hill Health Professions Division (2003) pp. 688-696.
2. Lonne-Rahm S B, Fischer T, Berg M. Stinging and rosacea. Acta Derm Venereol 1999; 79:460-461.
3. Wilkin J, Dahl M, Detmar M, et al. Standard grading system for rosacea: report of the National Rosacea Society Expert Committee on the Classification and Staging of Rosacea. J Am Acad Dermatol 2004; 50:907-912.
4. Griffiths W A. The red face—an overview and delineation of the MARSH syndrome. Clin. Exp Dermatol. 1999; 24:42-47.
5. Draelos Z D. Assessment of skin barrier function in rosacea patients with a novel 1% metronidazole gel. J Drugs Dermatol. 2005; 4:557-562.
6. Chen A Y, Zirwas M J. Steroid-induced rosacealike dermatitis: case report and review of the literature. Cutis. 2009 83(4):198-204.
7. Lee D H, Li K, Suh D H. Pimecrolimus 1% cream for the treatment of steroid-induced rosacea: an 8-week split-face clinical trial. Br J Dermatol. 2008; 158(5):1069-76.
8. Wollenberg A, Kroth J, Hauschild A, Dirschka T. Cutaneous side effects of EGFR inhibitors—appearance and management. Dtsch Med Wochenschr. 2010; 135(4):149-54.
9. Lacouture M E, Maitland M L, Segaert S, et al. A proposed EGFR inhibitor dermatologic adverse event-specific grading scale from the MASCC skin toxicity study group. Support Care Cancer. 2010; 18(4):509-22.
10. Palleschi G M, Torchia D. Rosacea in a monozygotic twin. Australas J Dermatol. 2007; 48:132-133.
11. Yazici A C, Tamer L, lkizoglu G, Kaya T I, Api H, Yildirim H, Adiguzel A. GSTM1 and GSTT1 null genotypes as possible heritable factors of rosacea. Photodermatol Photoimmunol Photomed. 2006; 22:208-210.
12. Jansen T, Plewig G. Rosacea: classification and treatment. J R Soc Med. 1997; 90:144-150.
13. Wilkin J K. Rosacea. Pathophysiology and treatment. Arch Dermatol. 1994; 130:359-362.
14. Forton F, Seys B: density of *Demodex folliculorum* in rosacea: A case-control study using standardized skin-surface biopsy. Br J Dermatol. 1993; 128:650.
15. Yamasaki K, Di Nardo A, Bardan A, Murakami M, Ohtake T, Coda A, Dorschner R A, Bonnart C, Descargues P, Hovnanian A, Morhenn V B, Gallo R L. Increased serine protease activity and cathelicidin promotes skin inflammation in rosacea. Nat Med. 2007; 13:975-980.
16, Zuyderduyn S, Ninaber D K, Hiemstra P S, Rabe K F. The antimicrobial peptide LL-37 enhances IL-8 release by human airway smooth muscle cells. Allergy Clin Immunol. 2006; 117:1328-1335.
17. Afonso A A, Sobrin L, Monroy D C, Selzer M, Lokeshwar B, Pflugfelder S C. Tear fluid gelatinase B activity correlates with IL-1alpha concentration and fluorescein clearance in ocular rosacea. Invest Ophthalmol Vis Sci. 1999; 40:2506-2512.
18. Pu L L, Smith P D, Payne W G, Kuhn M A, Wang X, Ko F, Robson M C. Overexpression of transforming growth factor beta-2 and its receptor in rhinophyma: an alternative mechanism of pathobiology. Ann Plast Surg. 2000; 45:515-519.
19. Guarrera M, Parodi A, Cipriani C, et al. Flushing in rosacea: a possible mechanism. Arch Dermatol Res. 1982; 272:311-316.
20. Smith J R, Lanier V B, Braziel R M, Falkenhagen K M, White C, Rosenbaum J T. Expression of vascular endothelial growth factor and its receptors in rosacea. Br J Ophthalmol. 2007; 91:226-229.
21. McDonnell J K, Tomecki K J. Rosacea: an update. Clev Clinic J Med. 2000; 67:587-590.
22. Gupta A K, Gover M D. Azelaic acid (15% gel) in the treatment of acne rosacea. Int J Dermatol. 2007; 46:533-538.
23. Berberine (2000). Altern Med Rev. 5:175-177
24. Yu H H, Kim K J, Cha J D, et al. Antimicrobial activity of berberine alone and in combination with ampicillin or oxacillin against methicillin-resistant *Staphylococcus aureus*. J Med Food. 2005; 8:454-461.
25. Mantena S K, Sharma S D, Katiyar S K. Berberine, a natural product, induces G1-phase cell cycle arrest and caspase-3-dependent apoptosis in human prostate carcinoma cells. Mol. Cancer Ther. 2006; 5:296-308.
26. Kuo C L, Chi C W, Liu T Y. The anti-inflammatory potential of berberine in vitro and in vivo. Cancer Lett. 2004; 203:127-137.
27. Khosla P K, Neeraj V I, Gupta S K, Satpathy G. Berberine, a potential drug for trachoma. Rev Int Trach Pathol Ocul Trop Subtrop Sante Publique. 1992; 69:147-65.
28. Meisner; Lorraine Faxon. Topical composition for the treatment of psoriasis and related skin disorders. U.S. Pat. No. 6,440,465 (2002).
29. Goodless, Dean R. Composition and method for treatment of acne. United States Patent Application 20050158404 (2005).
30. Lintner; Karl. Compositions containing mixtures of tetrapeptides and tripeptides. U.S. Pat. No. 6,974,799 (2005).

31. Gupta, Shyam K. Topical nutraceutical compositions with selective body slimming and tone firming antiaging benefits. United States Patent Application 20040146539 (2004).
32. Gulliver W P, Donsky H J. A report on three recent clinical trials using *Mahonia aquifolium* 10% topical cream and a review of the worldwide clinical experience with *Mahonia aquifolium* for the treatment of plaque psoriasis. Am J Ther. 2005; 12:398-406.
33. Iwasa K, et al. Fungicidal and herbicidal activities of berberine related alkaloids. Biosci. Biotechnol. Biochem. 2000; 64:1998-2000.
34. Iwasa K, Nanba H, Lee D U, Kang S I. Structure-activity relationships of protoberberines having antimicrobial activity. Planta Med. 1998; 64:748-751.
35. Prabal Giri, Maidul Hossain and Gopinatha Suresh Kumar. RNA specific molecules: Cytotoxic plant alkaloid palmatine binds strongly to poly(A). Bioorganic & Medicinal Chemistry Letters. 2006; 16:2364-2368.
36. Colombo M. L. et al. Cytotoxicity evaluation of natural coptisine and synthesis of coptisine from Berberine. Farmaco 2001; 56:403-409.
37. Chun-Ching Lin et al. Cytotoxic effects of *Coptis chinensis* and Epimedium sagittatum extracts and their major constituents (berberine, coptisine and icariin) on hepatoma and leukaemia cell growth. Clinical and Experimental Pharmacology and Physiology 2004; 31:65-69.
38. Thiboutot D, Thieroff-Ekerdt R, Graupe K. Efficacy and safety of azelaic acid (15%) gel as a new treatment for papulopustular rosacea: results from two vehicle-controlled, randomized phase III studies. J Am Acad Dermatol 2003; 48:836-845.

What is claimed is:

1. A method for treating a red face related skin disorder in a patient in need thereof, comprising topically applying to affected skin of said patient a therapeutically effective amount of a pharmaceutical composition comprising at least 0.1% w/w of berberine or pharmaceutically acceptable salt thereof, and wherein the said berberine or said pharmaceutically acceptable salt is the only active component, and wherein the red face related skin disorder is selected from the group consisting of rosacea, acne vulgaris, seborrheic dermatitis, photo dermatitis, contact dermatitis, steroid-induced rosacea-like dermatitis and EGFR inhibitors-induced acneiform dermatitis.

2. The method of claim 1, wherein the pharmaceutical composition comprises 0.1% to about 2% w/w of berberine or pharmaceutically acceptable salts thereof.

3. A method for treating a red face related skin disorder in a patient in need thereof, comprising topically applying to affected skin of said patient a therapeutically effective amount of a pharmaceutical composition comprising at least 0.02% w/w of palmatine or pharmaceutically acceptable salt thereof, and wherein the said palmatine or said pharmaceutically acceptable salt is the only active component, and wherein the red face related skin disorder is selected from the group consisting of rosacea, acne vulgaris, seborrheic dermatitis, photo dermatitis, contact dermatitis, steroid-induced rosacea-like dermatitis and EGFR inhibitors-induced acneiform dermatitis.

4. The method of claim 3, wherein the pharmaceutical composition comprises 0.02% to about 2% w/w of palmatine or pharmaceutically acceptable salts thereof.

* * * * *